(12) United States Patent
Huang et al.

(10) Patent No.: US 8,991,234 B2
(45) Date of Patent: Mar. 31, 2015

(54) VALPROIC ACID BIOSENSOR AND METHOD FOR MEASURING CONCENTRATION OF VALPROIC ACID

(71) Applicant: National Taiwan University, Taipei (TW)

(72) Inventors: Long-Sun Huang, Taipei (TW); Kai-Fung Chang, Taipei (TW); Yu-Chen Chang, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 13/956,259

(22) Filed: Jul. 31, 2013

(65) Prior Publication Data

US 2014/0209484 A1    Jul. 31, 2014

(30) Foreign Application Priority Data

Jan. 28, 2013 (TW) .............................. 102103203 A

(51) Int. Cl.
| | | |
|---|---|---|
| G01N 29/00 | (2006.01) | |
| G01N 29/02 | (2006.01) | |
| G01N 29/04 | (2006.01) | |
| G01N 29/22 | (2006.01) | |
| G01N 29/24 | (2006.01) | |
| G01N 27/414 | (2006.01) | |
| G01N 33/94 | (2006.01) | |

(52) U.S. Cl.
CPC ........ G01N 27/4145 (2013.01); G01N 33/9473 (2013.01)

USPC ............ 73/24.06; 73/23.2; 73/24.01; 422/50; 422/68.1; 422/82.01; 422/82.02

(58) Field of Classification Search
USPC .............................. 73/24.01–24.06; 422/68.1
See application file for complete search history.

(56) References Cited

U.S. PATENT DOCUMENTS

| 7,730,767 B2 | 6/2010 | Huang et al. |
| 8,169,124 B2 | 5/2012 | Lee et al. |

FOREIGN PATENT DOCUMENTS

TW         I346777         2/2009

OTHER PUBLICATIONS

Stubbs, Desmond D., Sang-Hun Lee, and William D. Hunt. "Vapor phase detection of a narcotic using surface acoustic wave immunoassay sensors."Sensors Journal, IEEE 5.3 (2005): 335-339.*

* cited by examiner

*Primary Examiner* — Paul Hyun
*Assistant Examiner* — Robert Eom
(74) *Attorney, Agent, or Firm* — Huffman Law Group, PC

(57) ABSTRACT

The present disclosure relates to a valproic acid biosensor. In some embodiments, the valproic acid biosensor may comprise a microcantilever, a self-assembly monolayer, and a valproic acid antibody layer. The self-assembly monolayer may immobilize on the microcantilever surface. The valproic acid antibody layer may immobilize on the self-assembly monolayer. The valproic acid antibody layer may be used to bind with valproic acid drug samples. The present disclosure further relates to methods for measuring the concentration of valproic acid drug samples.

11 Claims, 11 Drawing Sheets

US 8,991,234 B2

VALPROIC ACID BIOSENSOR AND METHOD FOR MEASURING CONCENTRATION OF VALPROIC ACID

CROSS-REFERENCE TO RELATED APPLICATION(S)

This application claims priority of Taiwan Patent Application No. 102103203, filed on Jan. 28, 2013, the disclosure of which is hereby incorporated by reference in its entirety.

FIELD OF THE DISCLOSURE

The present disclosure relates, in some embodiments, to a biosensor. More specifically, the present disclosure relates, in some embodiments, to a microcantilever biosensor.

BACKGROUND OF THE DISCLOSURE

Valproic acid is one of the most widely used antiepileptic drugs. To be effective as a remedy, the concentration of valproic acid in the blood vessels must be kept within a suitable range. Ineffective treatment may occur if the treatment dosage is too low. Even worse, adverse effects may occur if the treatment dosage is too high. Therefore, the concentration of the valproic acid in the blood vessels is very important.

The size of the instruments used to monitor the concentration of valproic acid may be large. Thus, the monitoring instruments may not be portable and their prices may be very expensive. Consequently, patients cannot immediately determine whether or not the concentration of the drug in their blood vessels is within the optimal range for effective treatment.

SUMMARY

Accordingly, there exists a need for an improved valproic acid biosensor that can address the aforementioned drawbacks.

The present disclosure relates, in some embodiments, to a valproic acid biosensors and methods for measuring the concentration of valproic acid in the blood vessels. Some embodiments of the present disclosure relate to valproic acid biosensors that may be small in size and may thus be portable for a point-of-care platform and personal diagnosis. As a result, patients may, anytime and anywhere, use the biosensor to assess their health and determine whether or not the concentration of valproic acid in their blood vessels is within the optimal range for effective treatment.

Some embodiments of the present disclosure relate to a valproic acid biosensor. The valproic acid biosensor may comprise a microcantilever, a self-assembly monolayer, and a valproic acid antibody layer. The self-assembly monolayer may be immobilized on the microcantilever surface. The valproic acid antibody layer may be immobilized on the self-assembly monolayer. The valproic acid antibody layer may be used to bind with valproic acid drug samples.

Some embodiments of the present disclosure relate to methods for measuring the concentration of the valproic acid in blood vessel. A method may comprise: manufacturing a microcantilever with a piezoresistive layer; binding a plurality of self-assembly molecules to the microcantilever; activating the self-assembly molecules bonded to the microcantilever; binding a plurality of valproic acid antibodies with the activated self-assembly molecules; binding a plurality of valproic acid drug samples with the valproic acid antibodies; measuring a change of resistance of the piezoresistive layer; and calculating the concentration of valproic acid according to a previously established relationship between the measured resistance change and the concentration of the valproic acid drug samples.

Some embodiments of the present disclosure relate to methods for measuring the concentration of the valproic acid in blood vessel. The steps of the method may comprise: manufacturing a microcantilever with a field effect transistor; binding a plurality of self-assembly molecules to the microcantilever; activating the self-assembly molecules bonded to the microcantilever; binding a plurality of valproic acid antibodies with the activated self-assembly molecules; binding a plurality of valproic acid drug samples with the valproic acid antibodies; measuring a change of current of the field effect transistor; and calculating the concentration of valproic acid according to the previously established relationship between the measured current change and the concentration of the valproic acid drug samples.

DETAILED DESCRIPTION

Figure 1:
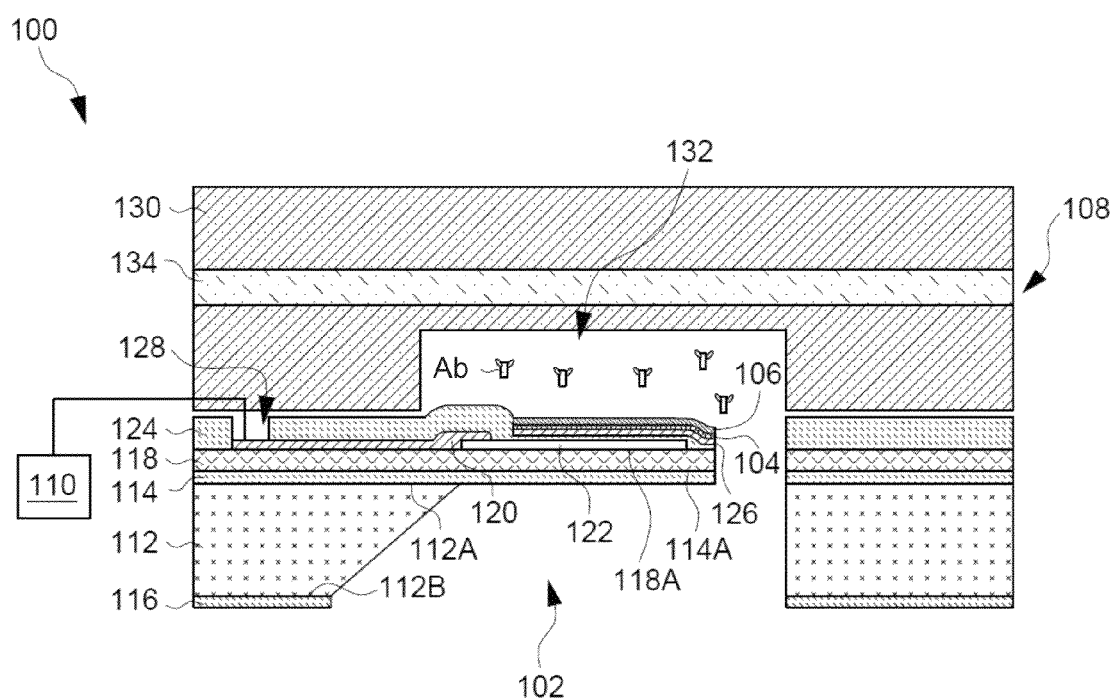
FIG. 1 illustrates a schematic view of a valproic acid biosensor according to some example embodiments of the disclosure.

FIG. 1 is a schematic view illustrating one embodiment of a valproic acid biosensor 100. As shown in FIG. 1, the valproic acid biosensor 100 may comprise a microcantilever 102, a self-assembly monolayer 104, and a valproic acid antibody layer 106, a microchannel 108, and a measuring equipment 110. The microcantilever 102 may include a substrate 112, which may be made of silicon. A passivating layer 114 may be deposited on a top surface 112A of the substrate 112, and a passivation layer 116 may be deposited on a bottom surface 112B of the substrate 112. The passivation layer 114 may also be used as a structural layer of the microcantilever. The passivation layers 114 and 116 may be made of $Si_3N_4$. A stress balance layer 118 may be deposited on a top surface 114A of the passivation layer 114, and the stress balance layer 118 may be made of $SiO_2$. A conducting wire 120, a piezoresistive layer 122, and a passivation layer 124 may be deposited on a top surface 118A of the stress balance layer 118. The conducting wire 120 may be made of Au and may be in contact with the piezoresistive layer 122. The passivation layer 124 may be made of $Si_3N_4$ and may cover the conducting wire 120. There may be a hole 128 on one end of the passivation layer 124. One end of the conducting wire 20 may be exposed through the hole 128 and may be connected with the measuring equipment 110. One end of the passivation layer 124 may be connected with the piezoresistive layer 122 and the stress balance layer 118. A sensing layer 126 may be deposited on a top surface of the passivation layer 124 and may be disposed above the piezoresistive layer 122. The piezoresistive layer 122 may be made of polysilicon. The sensing layer 126 may be a gold film. In preferred embodiments, the thickness of the sensing layer 126 may be less than 100 nm. The microchannel 108 may include a top cover 130 and a channel 132, and there may be a conductive glass layer 134 among the top cover 130.

The self-assembly monolayer 104 (SAM) may be composed of a plurality of self-assembly molecules which may be 8-Mercaptooctanoic acid. The self-assembly monolayer 104 may be formed by binding the self-assembly molecules to the sensing layer 126. The valproic acid antibody layer 106 may be composed of a plurality of valproic acid antibodies (Ab) and may be formed by binding the valproic acid antibodies with the self-assembly monolayer 104. The microcantilever 102 may be covered in the microchannel 108, and a plurality of valproic acid drug samples (Analyte) may be injected into the microchannel 108 to bind with the valproic acid antibodies. The measuring equipment 110 may be connected with the conducting wire 120 and the piezoresistive layer 122. The measuring equipment may then be used to measure the change of the resistance of the piezoresistive layer 122 and to then determine the concentration of valproic acid based on the previously determined relationship between the change of the resistance and the concentration of the valproic acid drug samples.

Figure 2:
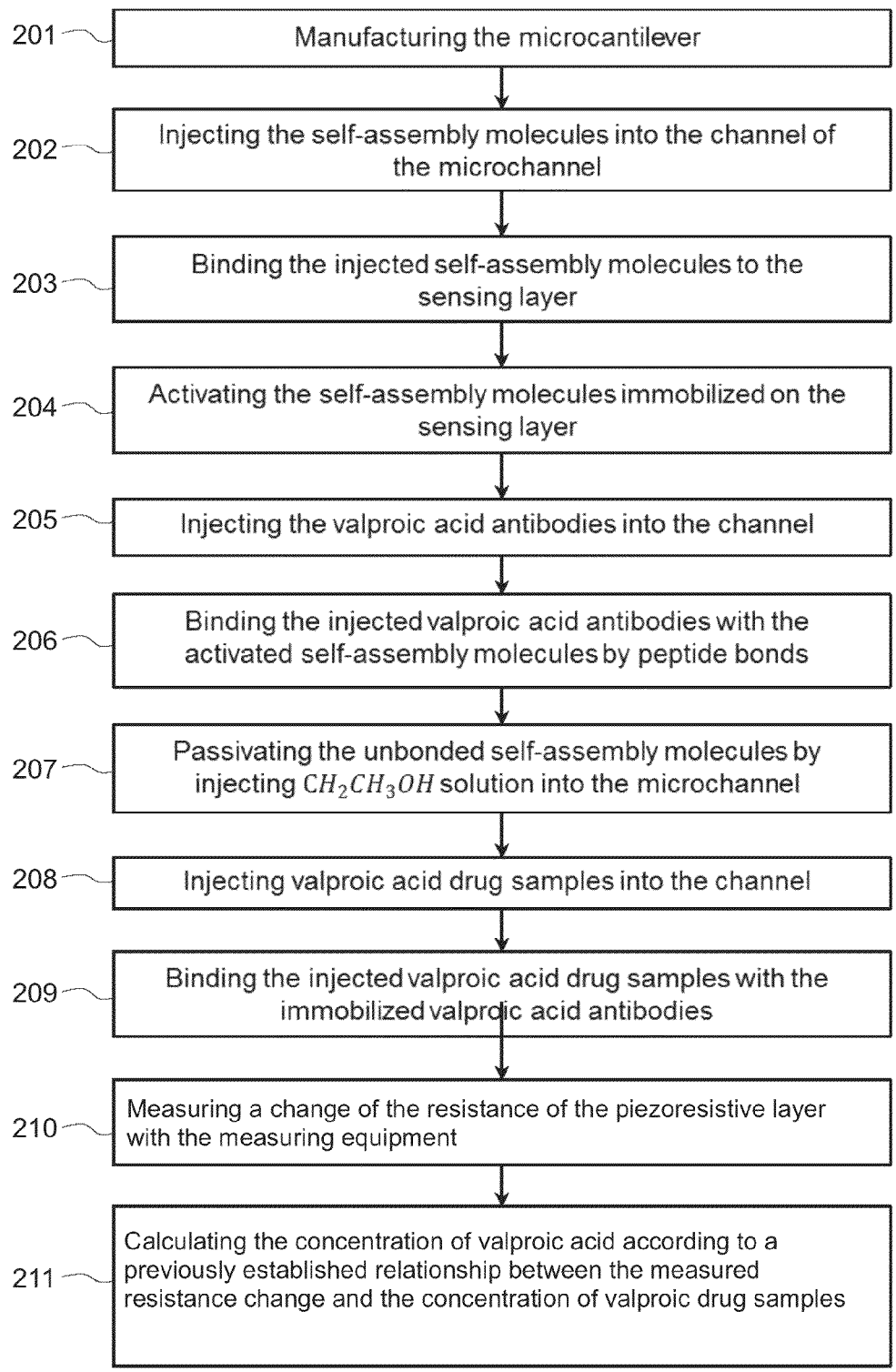
FIG. 2 illustrates a flowchart of one embodiment of a method for measuring the concentration of the valproic acid in blood vessel.

FIG. 2 is a flowchart illustrating one embodiment of a method for measuring the concentration of the valproic acid. As shown in FIG. 2, the steps of the method may comprise:

Step 201: Manufacturing the microcantilever 102;

Step 202: Injecting the self-assembly molecules into the channel 132 of the microchannel 108 since the valproic acid antibodies cannot bind directly to the sensing layer 126.

Step 203: The injected self-assembly molecules bind to the sensing layer 126. As a result, the self-assembly monolayer 104 may be formed.

Figure 3:
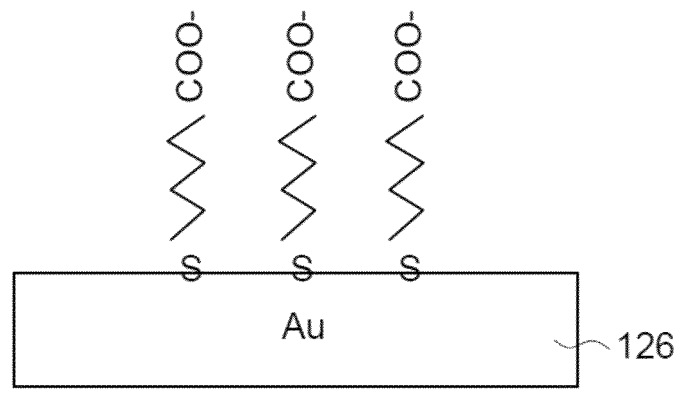
FIG. 3 illustrates a schematic view of self-assembly molecules binds to a microcantilever surface according to some example embodiments of the disclosure.

FIG. 3 is a schematic view illustrating the self-assembly molecules and the microcantilever 102. As shown in FIG. 3, the sulfur atom in self-assembly molecules may bond to and be immobilized on the sensing layer 126 by covalent bonds.

Figure 4:
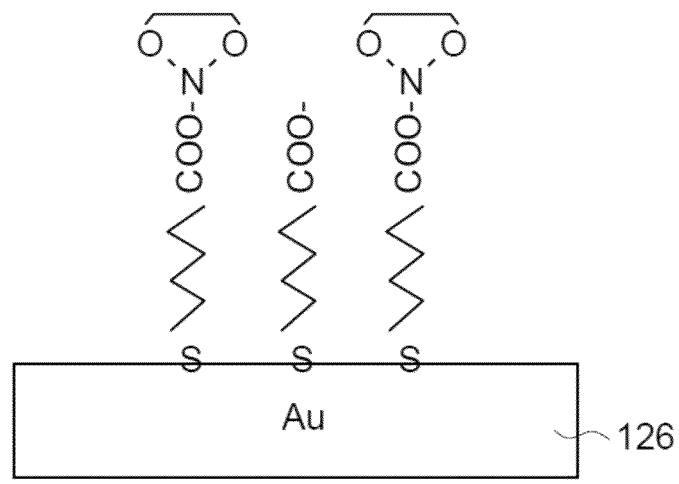
FIG. 4 illustrates a schematic view of the activation of self-assembly molecules according to some example embodiments of the disclosure.

Step 204: FIG. 4 is a schematic view of activation of the self-assembly molecules. As shown in FIG. 4, the self-assembly molecules immobilized on the sensing layer 126 may be activated, Thus, the self-assembly molecules may be bonded with the valproic acid antibodies.

Step 205: Injecting the valproic acid antibodies into the channel 132.

Step 206: The injected valproic acid antibodies may bind with the activated self-assembly molecules by peptide bonds. Subsequently, the valproic acid antibody layer 106 may be formed.

Figure 5:
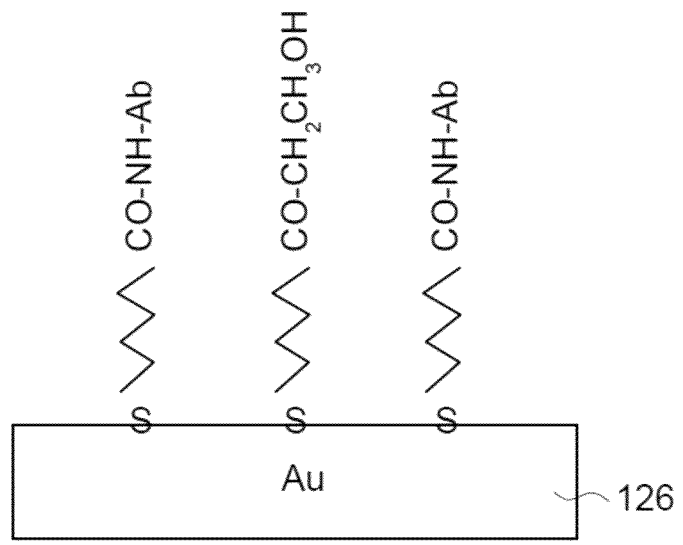
FIG. 5 illustrates a schematic view of valproic acid antibodies bonded with self-assembly molecules.

Step 207: FIG. 5 is a schematic view illustrating the passivating of the self-assembly molecules. Since not all of the self-assembly molecules are bonded with the injected valproic acid antibodies, passivating the self-assembly molecules which are not bonded to the valproic acid antibodies, passivating the unbonded self-assembly molecules by injecting $CH_2CH_3OH$ solution into the microchannel 108 may be necessary. Subsequently, the passivated self-assembly molecules may not be bonded with other molecules.

Figure 6:
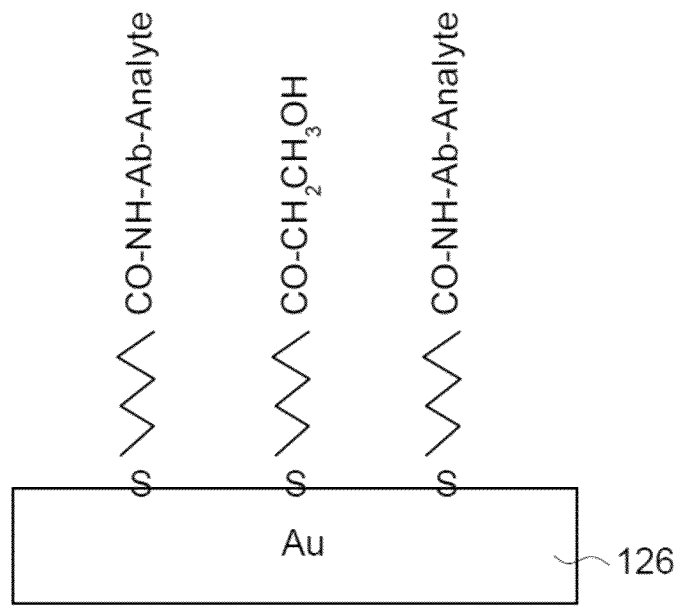
FIG. 6 illustrates a schematic view of valproic acid antibodies bonded with valproic acid drug samples according to some example embodiments of the disclosure.

Step 208: FIG. 6 is a schematic view of the immobilized the valproic acid antibodies and valproic acid drug samples. Injecting valproic acid drug samples into the channel 132.

Step 209: The injected valproic acid drug samples may bind with the immobilized valproic acid antibodies.

Step 210: Measuring a change of the resistance of the piezoresistive layer 122 with the measuring equipment 110.

Step 211: The concentration of valproic acid may be calculated according to the previously determined relationship between the measured resistance change and the concentration of valproic drug samples.

One of ordinary skill in the art having the benefit of the instant disclosure would appreciate that the resistance of the microcantilever 102 may be measured and that the surface stress of the piezoresistive layer 122 may be calculated. The measurements and calculations may occur during the Steps 202, 204, 207. Accordingly, one of ordinary skill in the art having the benefit of the instant disclosure may ensure that the immobilized valproic acid antibodies on the valproic acid biosensor 100 and the valproic acid drug samples change the surface stress of the microcantilever 102 and the resistance of the piezoresistive layer 122.

Figure 7:
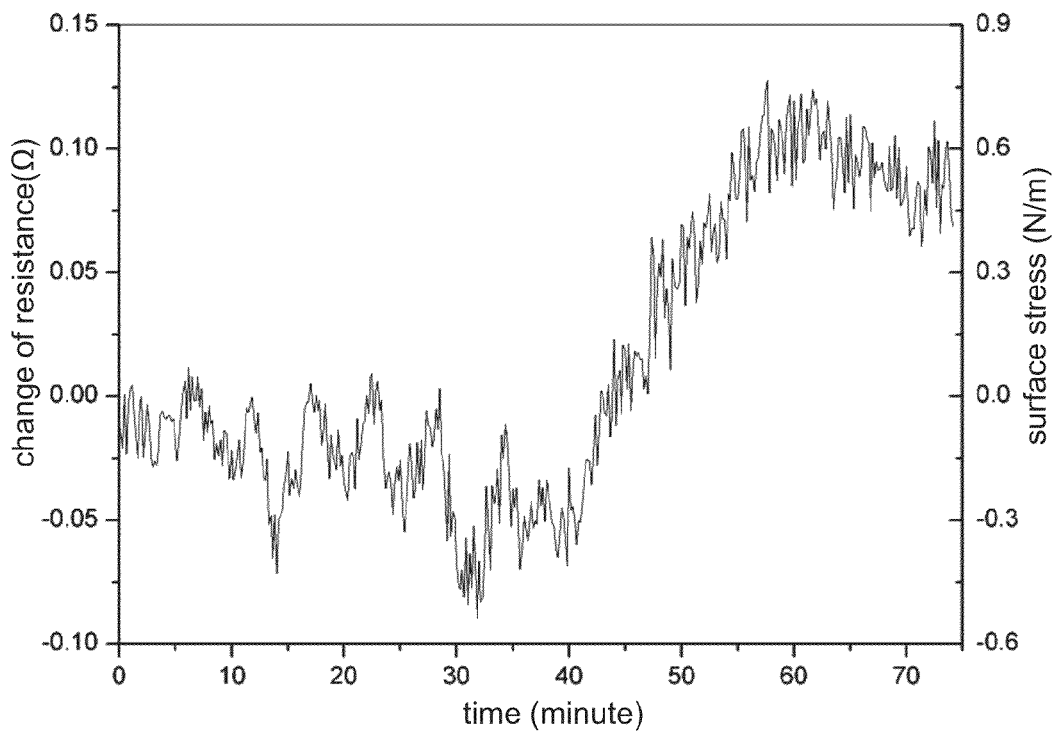
FIG. 7 illustrates changes in resistance and surface stress of a microcantilever after self-assembly molecules bind to a microcantilever according to some example embodiments of the disclosure.

FIG. 7 illustrates the changes in resistance and the surface stress change after the self-assembly molecules bind to the microcantilever 102. As shown in FIG. 7, when the self-assembly molecules bind to the sensing layer 126 of the microcantilever 102 by a covalent bond, the surface stress of the microcantilever 102 may be changed to 0.6 N/m and the piezoresistive layer 122 may be deformed due to the change of the surface stress. This change in the surface stress may subsequently cause the change of the resistance of the piezoresistive layer 122 by $0.1\Omega$.

Figure 8:
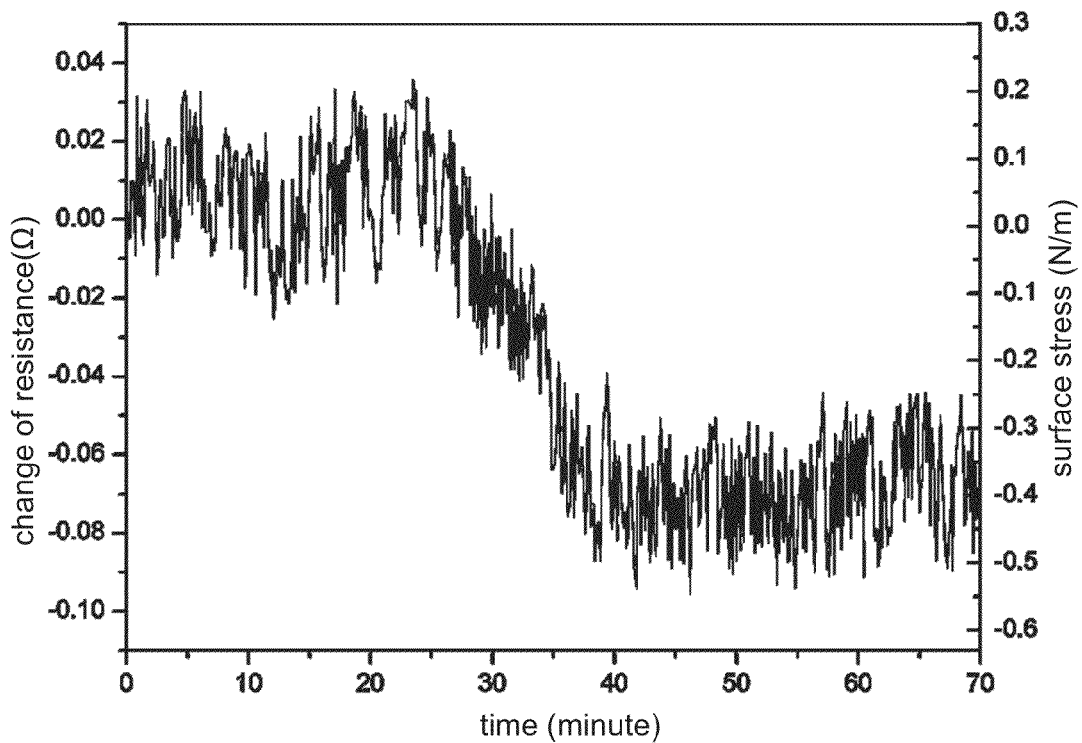
FIG. 8 illustrates changes in resistance and surface stress of a microcantilever after valproic acid antibodies bind with self-assembly molecules according to some example embodiments of the disclosure.

FIG. 8 illustrates the changes in resistance and the surface stress after binding the valproic acid antibodies to the microcantilever 102. As shown in FIG. 8, the valproic acid antibodies may bind with self-assembly molecules by peptide bonds. Accordingly, the surface stress of the microcantilever 102 may be changed to −0.48 N/m and the piezoresistive layer 122 may be deformed due to the change of the surface stress. This change in the surface stress may cause a change in the resistance of the piezoresistive layer 122 by 0.08Ω.

Figure 9:
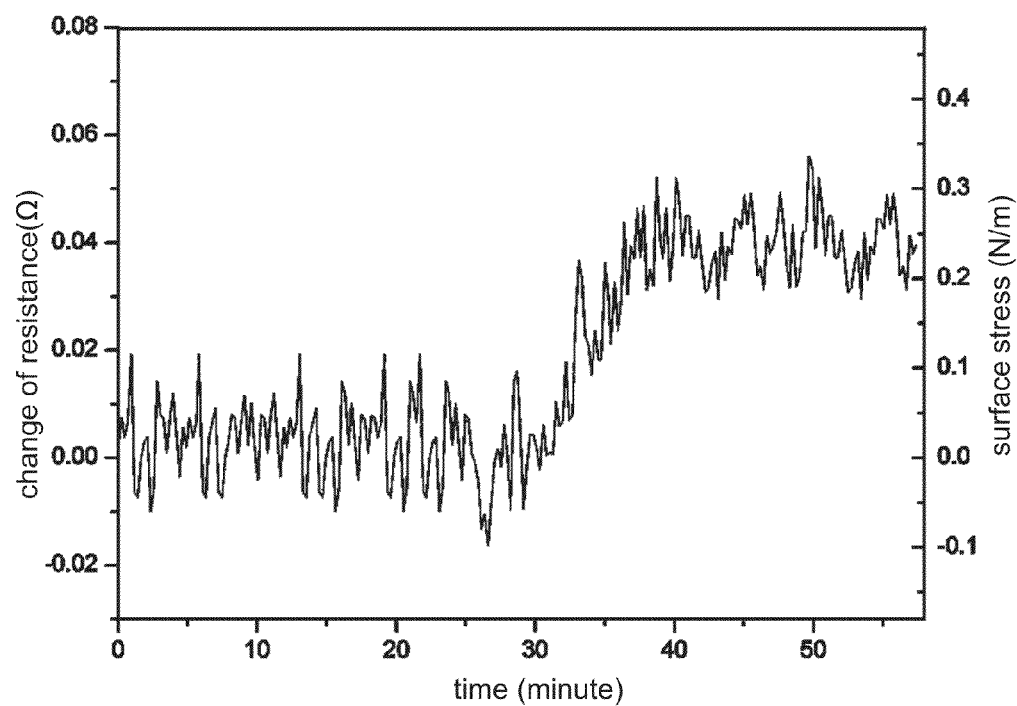
FIG. 9 illustrates changes in the resistance and surface stress of a microcantilever after valproic acid drug samples bind to the microcantilever according to some example embodiments of the disclosure.

FIG. 9 illustrates the changes in resistance and surface stress after binding the valproic acid drug samples to the microcantilever 102. As shown in FIG. 9, the valproic acid drug samples and the valproic acid antibodies may change the surface stress of the microcantilever 102. The piezoresistive layer 122 may be deformed due to the change in surface stress. The surface stress may be changed to 0.24 N/m, and the resistance of the piezoresistive layer 122 may changed by 0.04Ω due to this deformation.

Figure 10:
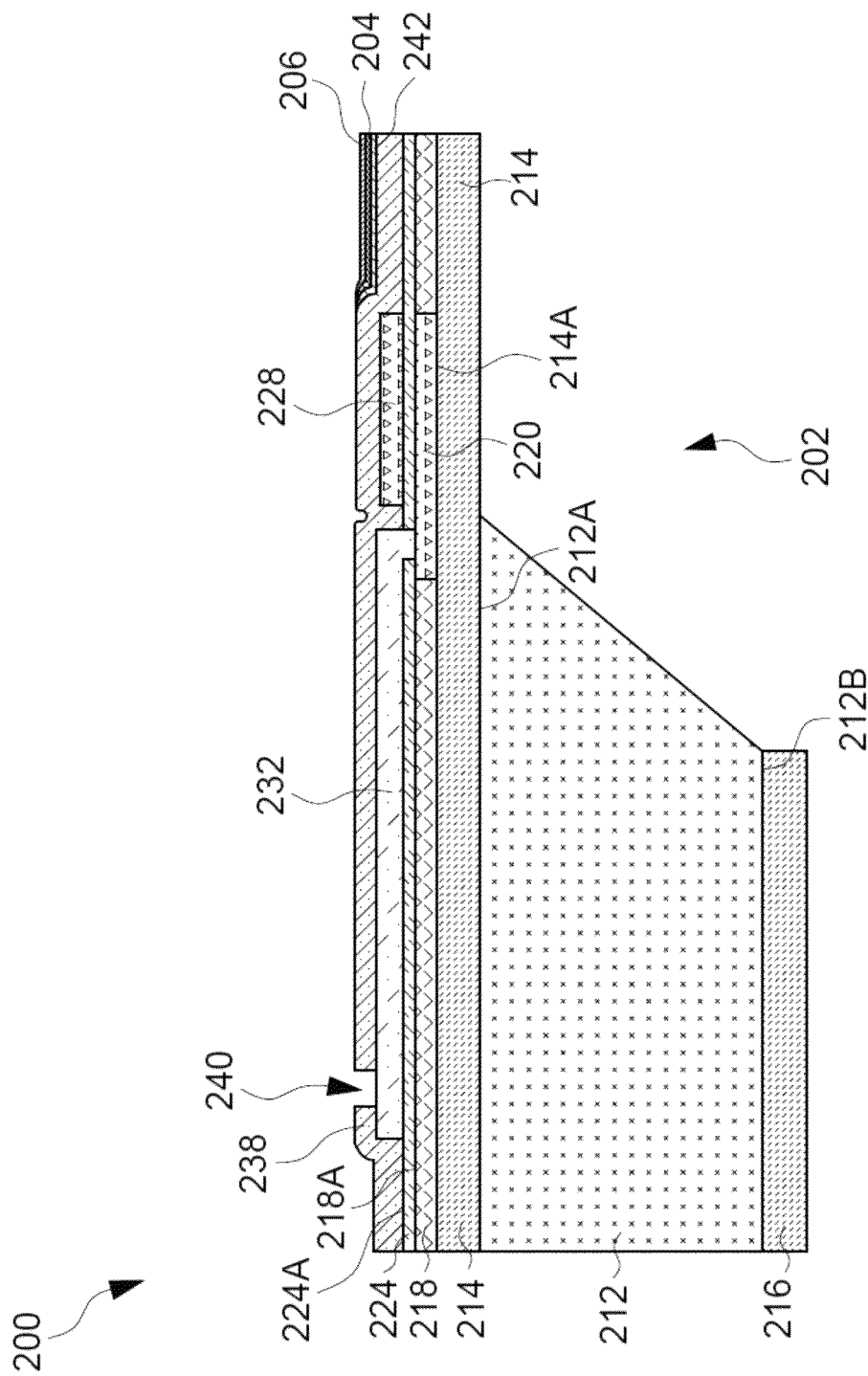
FIG. 10 illustrates a side view of a valproic acid biosensor according to some example embodiments of the disclosure.
Figure 11:
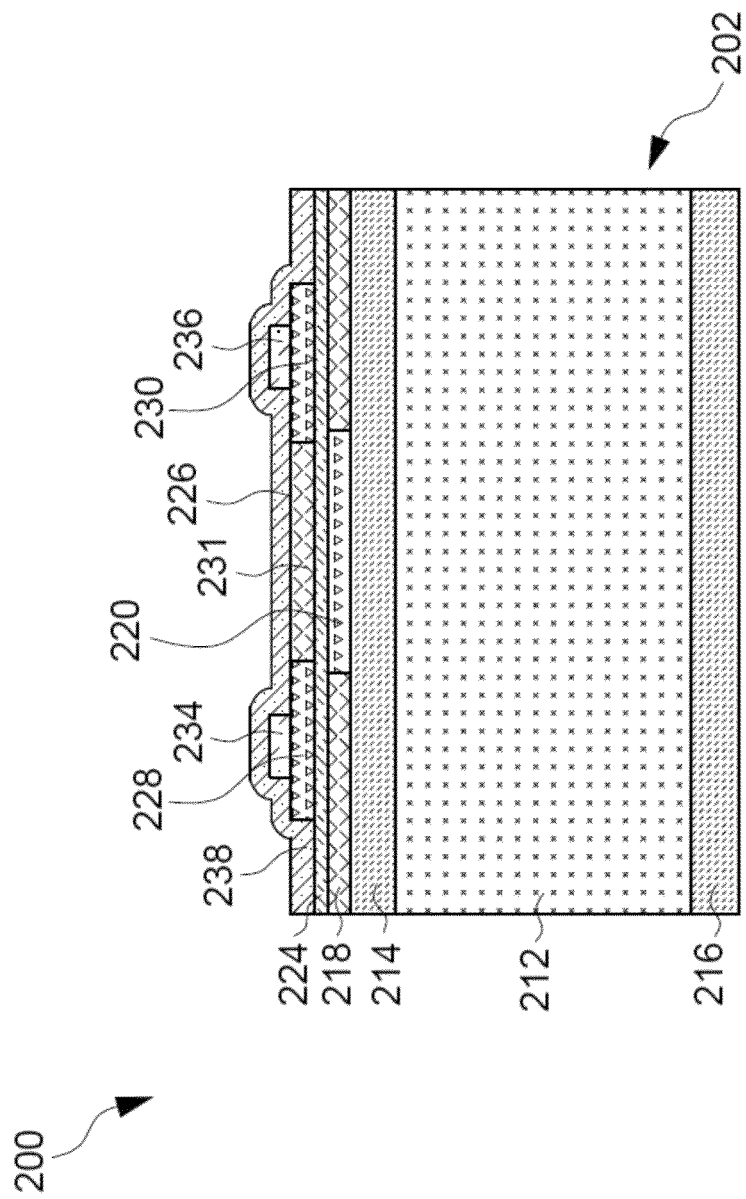
FIG. 11 illustrates a front view of the valproic acid sensor shown in FIG. 10.

FIGS. 10 and 11 illustrates a side view and front view, respectively, of a valproic acid biosensor 200 according to some example embodiments of the disclosure. In this embodiment, a field effect transistor type microcantilever may replace the piezoresistive type microcantilever in previously described embodiments. Accordingly, the same structures of the two embodiments are not described again as one of ordinary skill in the art would appreciate the other features in light of the previous descriptions in this disclosure. As shown in FIGS. 10 and 11, the valproic acid biosensor 200 may comprise a microcantilever 202, a self-assembly monolayer 204, and a valproic acid antibody layer 206. The microcantilever 202 may include a substrate 212, the substrate 212 may be made of silicon semiconductor doped with Boron or Phosphorous. A back side etching mask 214 may be deposited on an upper surface 212A of the substrate 212, and a lower passivation layer 216 may be deposited on a bottom surface 212B of the substrate 212. The back side etching mask 214 and the lower passivation layer 216 may be made of a Nitride, such as $Si_3N_4$. A first piezoresistive layer 218 may be deposited on an upper surface 214A of the back side etching mask 214, and the first piezoresistive layer 218 may be made of polysilicon. The first piezoresistive layer 218 may be doped with Phosphorous or Boron to form a gate electrode 220 of a field effect transistor. A dielectric layer 224 of the gate electrode 220 may be deposited on an upper surface 218A of the first piezoresistive layer 218, and the dielectric layer 224 can be made of $SiO_2$. A second piezoresistive layer 226, which may be made of polysilicon, may be deposited on an upper surface 224A of the dielectric layer 224, and the second piezoresistive layer 226 may be doped with Phosphorous or Boron to form a source electrode 228 and a drain electrode 230 of the field effect transistor. A channel 231 of the field effect transistor may be deposited between the source electrode 228 and the drain electrode 230, and the material of the channel 231 may be different from the materials of the source electrode 228 and the drain electrode 230. The doping material of the second piezoresistive layer 226 may not be directly related to the doping material of the first piezoresistive layer 218. A plurality of conductive wires 232, 234, 236 may be deposited on the upper surface 224A of the dielectric layer 224, and these conductive wires 232, 234, 236 may be in contact with the gate electrode 220, the source electrode 228, and the drain electrode 230, respectively. An upper passivation layer 238, which may be made of Nitride, may be deposited on the upper surface 224A of the dielectric layer 224, and the upper passivation layer 238 covers over the second piezoresistive layer 226, and the conductive wires 232, 234, 236. There may be three holes 240 at the end portion of the upper passivation layer 238, and the ends of the conductive wires 232, 234, 236 may be exposed through the holes 240, respectively, to allow for measuring of electrical signals (the electrical signal may be voltage or current) of field effect transistor. A sensing layer 242 may be deposited on a top surface of the upper passivation layer 238, and the sensing layer 242 may be made of a gold film. In some embodiments, the thickness of the sensing layer 242 may be less than 100 nm.

The self-assembly monolayer 204 may be composed of a plurality of 8-Mercaptooctanoic acid and may bind to the sensing layer 242 of the microcantilever 202. The valproic acid antibody layer 206 may be composed of a plurality of valproic acid antibodies and may bind with the self-assembly monolayer 204. After the injected valproic acid drug samples binds with the valproic acid antibody layer 206, the microcantilever 202 may be deformed. At the same time, the current of the field effect transistor may be changed if the voltages between gate electrode and drain electrode are kept constant. The concentration of the valproic acid may be calculated according to the previously determined relationship between the change of the current of the field effect transistor and the concentration of the valproic acid drug samples.

Figure 12:
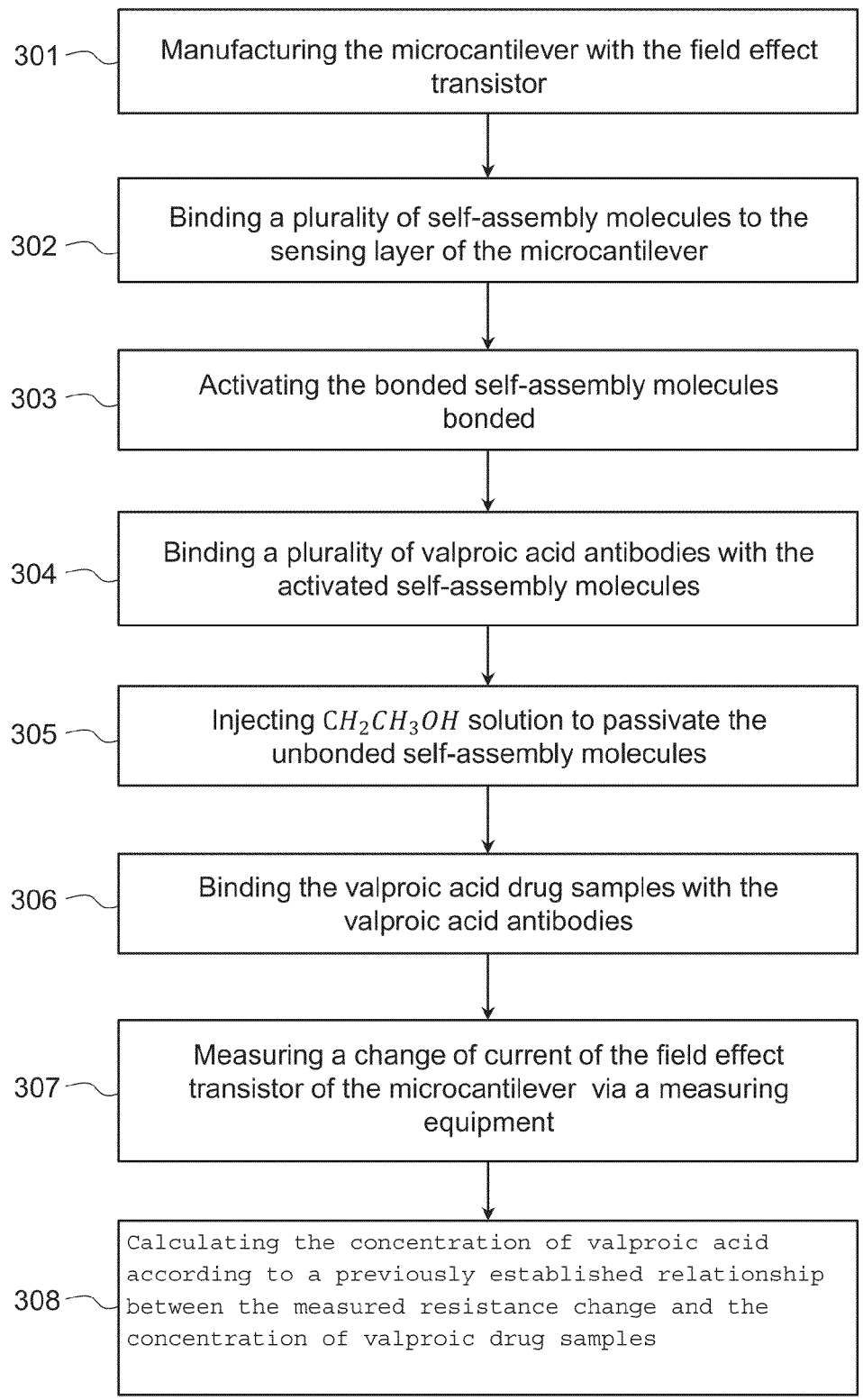
FIG. 12 illustrates a flowchart of an embodiment of a method for measuring the concentration of valproic acid in a blood vessel according to some example embodiments of the disclosure.

FIG. 12 is a flowchart illustrating another embodiment of a method for measuring the concentration of the valproic acid. As shown in FIG. 12, the steps of the method may comprise:

Step 301: Manufacturing the microcantilever 202 with the field effect transistor;

Step 302: A plurality of self-assembly molecules may bind to the sensing layer 242 of the microcantilever 202 since the valproic acid antibodies may not be directly bonded to the sensing layer 242 of the microcantilever 202. Subsequently, the self-assembly monolayer 204 may be formed.

Step 303: Activating the self-assembly molecules bonded to the sensing layer 242, and the self-assembly molecules may easily be bonded with the valproic acid antibodies.

Step 304: Binding a plurality of valproic acid antibodies with the activated self-assembly molecules, so that the valproic acid antibody layer 206 may be formed.

Step 305: Not all of the self-assembly molecules may be bonded with the valproic acid antibodies, injecting $CH_2CH_3OH$ solution to passivate the unbonded self-assembly molecules.

Step 306: Binding the valproic acid drug samples with the valproic acid antibodies.

Step 307: Measuring a change of the current of the field effect transistor of the microcantilever 202 via a measuring equipment.

Step 308: The concentration of valproic acid may be calculated according to a previously determined relationship between the measured current change and the concentration of valproic acid drug samples.

Figure 13:
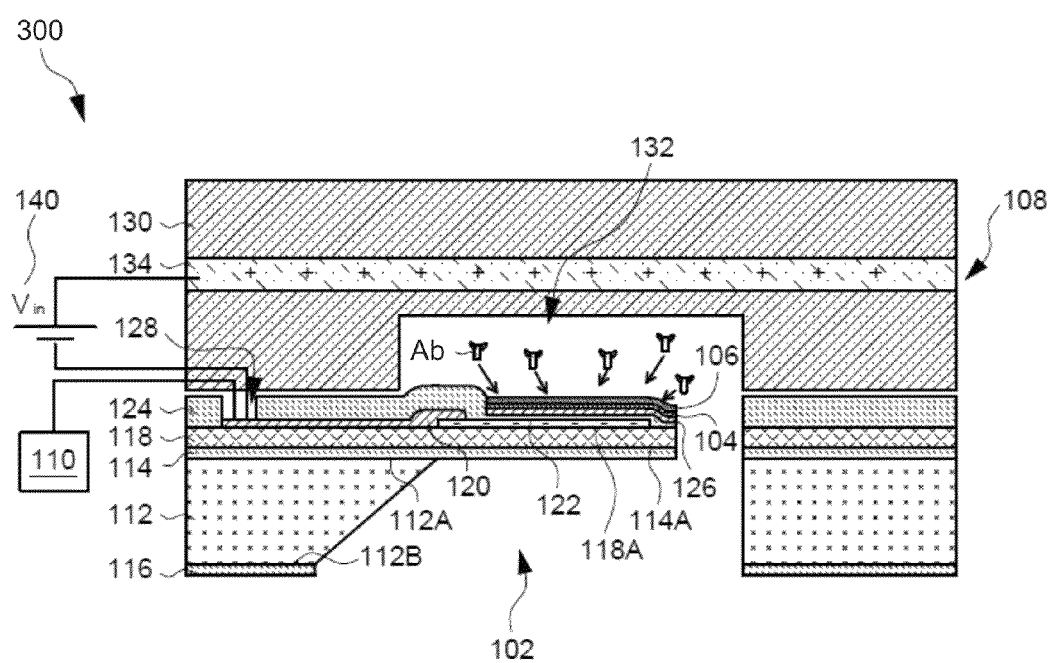
FIG. 13 illustrates a schematic view of a valproic acid biosensor according to some example embodiments of the disclosure.

FIG. 13 is a schematic view illustrating a valproic acid biosensor 300 according to some example embodiments of the disclosure. Valproic acid biosensor 300 may further comprises a power supply 140. The anode and the cathode of the power supply 140 may be connected with the conductive glass layer 134 and the piezoresistive layer 122, respectively. The power supply 140 may provide positive charges and negative charges to the conductive glass layer 134 and the piezoresistive layer 122, respectively. At this time, the negative and positive charges may cause an electrical filed in the channel 132 and the generated electrical field may point to the surface of microcantilever 102. The generated electrical filed may drive more valproic acid antibodies to move toward the microcantilever 102. Thus, more valproic acid antibodies may bind to the microcantilever 102.

Figure 14:
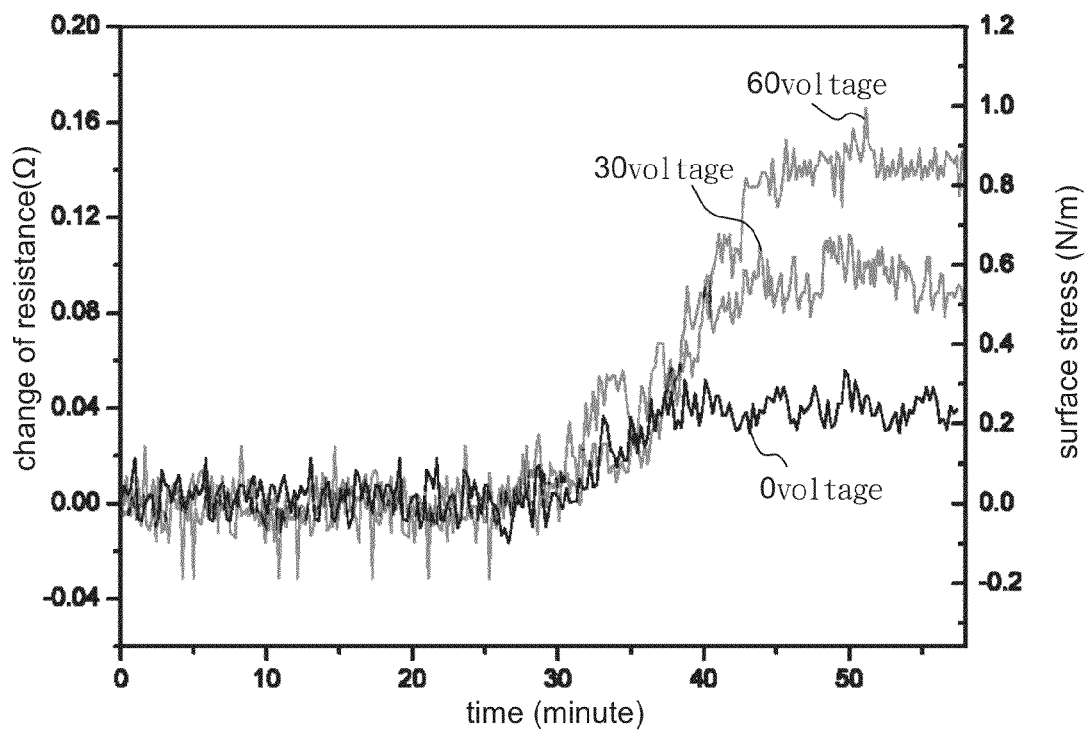
FIG. 14 illustrates the electric field strength according to different concentrations of the valproic acid drug samples according to some example embodiments of the disclosure.
Figure 15:
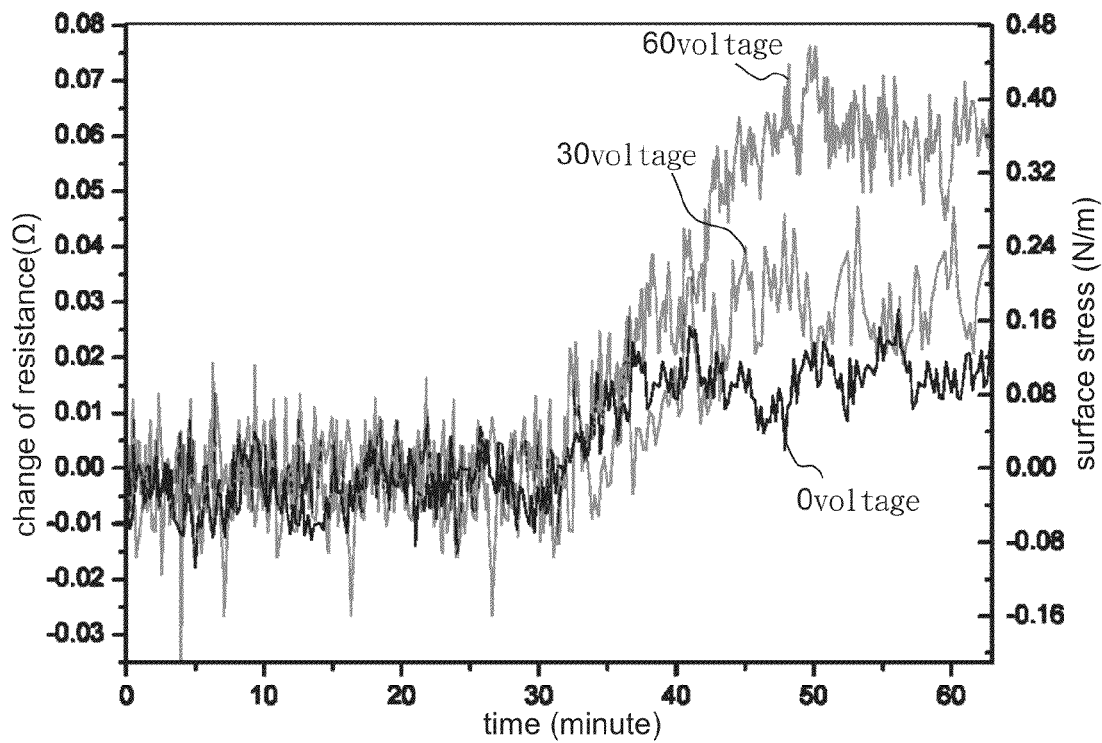
FIG. 15 illustrates the change of resistance according to different concentrations of the valproic acid drug samples according to some example embodiments of the disclosure.

FIGS. 14 and FIG. 15 illustrate the electrical field strength and the change in resistance according to different concentrations of the valproic acid drug samples. As shown in FIG. 14, the concentration of the valproic acid drug samples is 100 ug/ml. As shown in FIG. 15, the concentration of the valproic acid drug samples is 50 ug/ml. After injecting the valproic acid drug samples to the channel 132, the power supply 140 may be operated to provide different voltages to cause different strengths of electrical fields. When the strength of the electrical field increases, a response signal may increase as well since there are more valproic acid drug samples binding to the microcantilever 102. Therefore, the strength of the electrical field may be controlled to promote sensitivity of the valproic acid biosensor at the same concentration of the valproic acid drug samples.

One of ordinary skill having the benefit of the instant disclosure in the art would appreciate that the valproic acid biosensor 200 may also be coupled to the power supply 140. The power supply 140 may provide an electrical field that points to the microcantilever 202 and the generated electrical field may drive more valproic acid drug samples to bind to the microcantilever 202.

One of ordinary skill in the art having the benefit of the instant disclosure would appreciate that the valproic acid biosensor and the method for measuring the concentration of the valproic acid described in the present disclosure may provide for several advantages. For example, the size of the valproic acid biosensor may be sufficiently small to allow for increased portability and may allow for a point-of-care platform and personal diagnosis. As a result, patients may use the valproic acid biosensor to easily determine whether or not the concentration of the drug in their blood vessels is within the optimal range for effective treatment. As another example, the manufacturing costs for the valproic acid biosensor may be substantially cheaper.

Realizations in accordance with the present disclosure therefore have been described only in the context of particular embodiments. These embodiments are meant to be illustrative and not limiting. Many variations, modifications, additions, and improvements are possible and will become clear to one of ordinary skill in the art. Accordingly, plural instances may be provided for components described herein as a single instance. Structures and functionality presented as discrete components in the exemplary configurations may be implemented as a combined structure or component. These and other variations, modifications, additions, and improvements may fall within the scope of the invention as defined in the claims that follow.

What is claimed is:

1. A valproic acid biosensor comprising:
   a microcantilever;
   a self-assembly monolayer immobilized on the microcantilever; and
   a valproic acid antibody layer immobilized on the self-assembly monolayer and used for binding to valproic acid drug samples.

2. The valproic acid biosensor according to claim 1, further comprising a microchannel, wherein the microcantilever is covered in the microchannel, the valproic acid drug samples are injected to the microchannel and bind with the valproic acid antibody layer, the microchannel has a conductive glass layer, and the conductive glass layer is above the microcantilever.

3. The valproic acid biosensor according to claim 2, further comprising a power supply, a positive electrode of the power supply connected with the glass conductive layer, and a negative electrode of the power supply connected with a piezoresistive layer of the microcantilever.

4. The valproic acid biosensor according to claim 1, wherein the microcantilever includes a sensing layer and a piezoresistive layer, the self-assembly monolayer immobilizes on the sensing layer, and the piezoresistive layer is below the sensing layer.

5. The valproic acid biosensor according to claim 4, wherein the sensing layer is made of a gold film and the thickness of the sensing layer is thinner than 100 nm.

6. The valproic acid biosensor according to claim 4, wherein the piezoresistive layer is made of polysilicon.

7. The valproic acid biosensor according to claim 1, wherein the self-assembly monolayer is composed of a plurality of self-assembly molecules which are 8-Mercaptooctanoic acid.

8. A method for measuring a concentration of valproic acid, comprising:
   manufacturing a microcantilever having a piezoresistive layer;
   binding a plurality of self-assembly molecules to the microcantilever;
   activating the bonded self-assembly molecules;
   binding a plurality of valproic acid antibodies with the activated self-assembly molecules;
   binding a plurality of valproic acid drug samples with the valproic acid antibodies;
   measuring a change of resistance of the piezoresistive layer; and
   calculating the concentration of the valproic acid according to the relationship between the measured resistance change and the concentration of the valproic acid drug samples constructed previously.

9. The method according to claim 8, further providing a electrical field, and the electrical field points to the microcantilever.

10. The method according to claim 8, wherein self-assembly molecules which are not bonded with the valproic acid drug samples are passivated to prevent them from binding with other molecules.

11. The method according to claim 8, wherein unbonded self-assembly molecules are passivated injecting $CH_2CH_3OH$ solution.

* * * * *